(12) United States Patent
Deceglie et al.

(10) Patent No.: US 10,554,172 B2
(45) Date of Patent: Feb. 4, 2020

(54) ILLUMINATED OUTDOOR LUMINESCENCE IMAGING OF PHOTOVOLTAIC MODULES

(71) Applicant: Alliance for Sustainable Energy, LLC, Golden, CO (US)

(72) Inventors: Michael Gardner Deceglie, Golden, CO (US); Timothy J. Silverman, Golden, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 61 days.

(21) Appl. No.: 15/916,862

(22) Filed: Mar. 9, 2018

(65) Prior Publication Data

US 2018/0262159 A1    Sep. 13, 2018

Related U.S. Application Data

(60) Provisional application No. 62/469,026, filed on Mar. 9, 2017.

(51) Int. Cl.
*G01N 21/66* (2006.01)
*H02S 50/15* (2014.01)
*G01N 21/95* (2006.01)

(52) U.S. Cl.
CPC ............. *H02S 50/15* (2014.12); *G01N 21/66* (2013.01); *G01N 21/9501* (2013.01)

(58) Field of Classification Search
CPC .................................. H02S 50/15; G01N 21/66
See application file for complete search history.

(56) References Cited

U.S. PATENT DOCUMENTS

| | | | |
|---|---|---|---|
| 8,471,408 B2* | 6/2013 | Bundschuh | H01L 31/02021 307/151 |
| 9,641,125 B2 | 5/2017 | Johnston | |
| 2009/0000659 A1* | 1/2009 | Hasegawa | H01L 31/02021 136/252 |
| 2010/0126569 A1* | 5/2010 | Oh | H01L 31/02242 136/255 |
| 2011/0012636 A1 | 1/2011 | Carstensen et al. | |

(Continued)

FOREIGN PATENT DOCUMENTS

WO    WO 2010/130013 A1    11/2010

OTHER PUBLICATIONS

ARC Photovoltaics Centre of Excellence, University of NW South Wales, ARC Photovoltaics 2010/11 Annual Report, pp. 100-105.
(Continued)

*Primary Examiner* — Dominic E Hawkins
(74) *Attorney, Agent, or Firm* — Michael A. McIntyre

(57) ABSTRACT

The present disclosure relates to a method that includes applying a first condition to a photovoltaic (PV) device, and applying a second condition to the PV device, where the first condition results in a first luminescing of a surface of the PV device at a first intensity, the second condition results in a second luminescing of the surface at a second intensity, measuring the first intensity using a detector to create a first representation of the surface, measuring the second intensity using the detector to create a second representation of the surface, and comparing the first representation with the second representation to create a third representation of the surface that identifies a defect in the surface, if present.

11 Claims, 12 Drawing Sheets

(56) References Cited

U.S. PATENT DOCUMENTS

| | | | |
|---|---|---|---|
| 2012/0193512 A1* | 8/2012 | Wu | G01S 3/7861 |
| | | | 250/203.4 |
| 2014/0039820 A1 | 2/2014 | Trupke et al. | |
| 2015/0168303 A1* | 6/2015 | Trupke | G01N 21/6456 |
| | | | 324/762.01 |
| 2016/0056761 A1* | 2/2016 | Mabille | H02S 50/10 |
| | | | 356/237.1 |
| 2016/0084764 A1 | 3/2016 | Johnston | |
| 2016/0365833 A1* | 12/2016 | Saby | G01J 1/44 |
| 2017/0194901 A1* | 7/2017 | Seliger | H02S 40/34 |
| 2017/0279275 A1* | 9/2017 | Yamamoto | H02J 7/35 |
| 2018/0159468 A1* | 6/2018 | Trupke | H02S 50/15 |
| 2018/0159469 A1* | 6/2018 | Trupke | H02S 50/15 |

OTHER PUBLICATIONS

Benatto, G. et al., "Luminescence Imaging Strategies for Drone-Based PV Array Inspection," Proceedings of the 33rd European Photovoltaic Solar Energy Conference and Exhibition, 2017, 5 pages.

Bhoopathy, R. et al., "Outdoor photoluminescence imaging of photovoltaic modules with sunlight excitation," Wiley Photovoltaics Short Communications, Prog. Photovoltaics, Res, Appl, 2017, 5 pages.

Courtois, G. et al., "Investigation of silicon heterojunction solar cells by photoluminescence under DC-bias," EPJ Photovoltaics, vol. 4, 2013, pp. 45106-1 through 45106-5.

DeGraff, D. et al., "Degradation Mechanisms in Si Module Technologies Observed in the Field: Their Analysis and Statistics," NREL 2011 Photovoltaic Module Reliability Workshop, Golden, Colorado, Feb. 16, 2011, pp. 1-25.

Ebner, R. et al., "Non-destructive techniques for quality control of PV modules: infrared thermography, electro- and photoluminescence imaging," IECON 2013, 39th Annual Conference of IEEE, pp. 8104-8109.

Fuyuki, T. et al., "Photographic diagnosis of crystalline silicon solar cells utilizing electroluminescence," Applied Physics A, Materials Science & Processing, vol. 96, 2009, pp. 189-196.

Johnston, S. et al., "Correlations of Cu(In, Ga) Se$_2$ imaging with device performance, defects, and microstructural properties," Journal of Vacuum Science Technology A, vol. 30, No. 4, Jul./Aug. 2012, pp. 04D111-1 through 04D111-6.

Johnston, S. et al., "Photoluminescence and Electroluminescence Outdoor Module Imaging," Poster, 2015 PV Module Reliability Workshop, Golden, Colorado, Feb. 24, 2015, one page.

Jordan, D. et al., "Photovoltaic Degradation Rates—An Analytical Review," NREL/JA-5200-51664, Jun. 2012, pp. 1-32.

Kasemann et al., "Contactless Qualitative Series Resistance Imaging on Solar Cells," IEEE Journal of Photovoltaics, vol. 2, No. 2, Apr. 2012, pp. 181-183.

Liu, J. et al., "Non-contact Determination of Local Efficiency of Mc-Si Solar Cells Using Quantitative Lock-In Thermographic and Carrierographic (Photoluminescence) Imaging," published online Nov. 7, 2014, pp. 1-10.

Ott, T. et al., "2D network simulation and luminescence characterization of Cu(In, Ga)Se$_2$ thin film modules," Progress in Photovoltaics: Research and Applications, vol. 20, Issue 5, Aug. 2012, pp. 600-605.

Pingel, S. et al., "Initial Degradation of Industrial Silicon Solar Cells in Solar Panels," 25th EU-PVSEC, Sep. 6-9, 2010, Valencia, Spain, 6 pages.

Shinde, K. et al., Phosphate Phosphors for Solid-State Lighting, Chapter 2, "Basic Mechanisms of Photoluminescence," Springer Series in Materials Science, Springer-Verlag Berlin Heidelberg 2013, pp. 41-59.

Sinton, R., "Contactless Electroluminescence for Shunt-Value Measurement in Solar Cells," 23rd European Photovoltaic Solar Energy Conference, Sep. 1-5, 2008, Valencia, Spain, pp. 1157-1159.

Solar Zentrum Stuttgart, "Mobile ElectroLuminescence Inspection," https://web.archive.org/web/20130402084115/http://www.solarzentrum-stuttuart.com/handouts/19_MELI_handout.pdf (Online on Apr. 2, 2013).

Solar Zentrum Stuttgart, "PV Module Electroluminescence: Enlightening Defects," http://www.uspvmc.org/proceedings/Infrared_Thermography_Workshop_0711/4.%20Daylight%20Luminescence%20(DaySv).pdf (Last modified on Jul. 25, 2013).

Sopori, B. et al., "Understanding Light-Induced Degradation of c-Si Solar Cells," presented at the 2012 IEEE Photovoltaic Specialists Conference, Jun. 3-8, 2012, Austin, Texas, pp. 1-5 (NREL/CP-5200-54200 Jun. 2012).

Stoicescu, L. et al., "Daylight Luminescence for Photovoltaic System Testing," presented at 22nd Photovoltaic Science and Engineering Conference, Nov. 5-9, 2012, Hangzhou, China, 3 pages.

Stojan, R. et al., "Luminescence radiation spectroscopy of silicon solar cells," presented at the Proceedings of the SPIE, vol. 8825, Sep. 24, 2013, pp. 88250T-1 through 88250T-6.

International Search Report from PCT/US16/15130, dated Apr. 13, 2016, 5 pages.

Written Option from PCT/US16/15130, dated Apr. 13, 2016, 12 pages.

* cited by examiner

ILLUMINATED OUTDOOR LUMINESCENCE IMAGING OF PHOTOVOLTAIC MODULES

CROSS-REFERENCE TO RELATED APPLICATIONS

This application claims the benefit of U.S. Provisional Patent Application No. 62/469,026 filed Mar. 9, 2017, the contents of which are incorporated herein by reference in their entirety.

CONTRACTUAL ORIGIN

The United States Government has rights in this invention under Contract No. DEAC36-08GO28308 between the United States Department of Energy and the Alliance for Sustainable Energy, LLC, the Manager and Operator of the National Renewable Energy Laboratory.

BACKGROUND

Improvements in camera and computer technology have recently enabled the collection of electroluminescence (EL) images outdoors under solar illumination. Typical EL imaging requires a DC power supply unit (DC PSU) with a power output roughly equal to the nameplate power of the PV devices under test (DUT). It would be advantageous to develop a method of outdoor photoluminescence (PL) imaging that does not require such a power supply, as well as advanced methods that are portable and can be used during both daylight and dark conditions.

SUMMARY OF THE INVENTION

An aspect of the present disclosure is a method that includes applying a first condition to a photovoltaic (PV) device, and applying a second condition to the PV device, where the first condition results in a first luminescing of a surface of the PV device at a first intensity, the second condition results in a second luminescing of the surface at a second intensity, measuring the first intensity using a detector to create a first representation of the surface, measuring the second intensity using the detector to create a second representation of the surface, and comparing the first representation with the second representation to create a third representation of the surface that identifies a defect in the surface, if present.

In some embodiments of the present disclosure, the applying the first condition may include applying a first current to the PV device. In some embodiments of the present disclosure, the applying the second condition may include applying a second current to the PV device, where the second current is different from the first current. In some embodiments of the present disclosure, the applying the first condition may include drawing a third current from the PV device.

In some embodiments of the present disclosure, the applying the second condition may include drawing a fourth current from the PV device, where the fourth current is different from the third current. The method of claim 5, wherein the first current is achieved by short-circuiting the PV device, such that the first current is equal to the short-circuit current ($I_{sc}$) of the PV device. In some embodiments of the present disclosure, the second current may be achieved by regulating the second current to a value between 0.01 $I_{sc}$ and 0.99 $I_{sc}$. In some embodiments of the present disclosure, the second current may correspond to varying the second current between 0.01 $I_{sc}$ and 0.99 $I_{sc}$, where the second measuring is performed during at least a portion of the varying.

In some embodiments of the present disclosure, the method may further include a first switching between the first applying and the second applying, and a second switching between the second applying and the first applying, where the first condition is maintained for a first period of time, after the first period of time has ended, the first switching occurs, the second condition is maintained for a second period of time, after the second period of time has ended, the second switching occurs, and the first switching and the second switching are repeated between 1 and 1000 occurrences. In some embodiments of the present disclosure, at least one of the first luminescing and/or the second luminescing produces light may include a wavelength between 800 nm and 1300 nm. In some embodiments of the present disclosure, the method may further include filtering at least a portion of the light. In some embodiments of the present disclosure, the applying the first condition and the applying the second condition may be performed while the surface is exposed to sunlight.

An aspect of the present disclosure is a system that includes a switch and a detector, where the switch is configured to be electrically connected to a photovoltaic (PV) device, the PV device is configured to generate a current, the switch has a first position that results in the PV device being short-circuited, resulting in a short-circuit current, $I_{sc}$, and the switch has a second position that results in the PV device providing a current, I, where $0 \leq I < I_{sc}$. In some embodiments of the present disclosure, the switch may include at least one of a MOSFET, a bipolar junction transistor, a silicon-controlled rectifier, a solid-state relay, an electromechanical relay, and/or a mechanical switch. In some embodiments of the present disclosure, the switch may be connected in series with the PV device. In some embodiments of the present disclosure, the system may further include at least one of a power supply and/or a power load, where the at least one of the power supply and or the power load, and the switch are electrically connected to the PV device in parallel.

In some embodiments of the present disclosure, the power load may include at least one of a direct current load, a programmable electronic load, a variable resistor, and/or a fixed resistor. In some embodiments of the present disclosure, the detector may include at least one of an Si camera and/or an InGaAs camera. In some embodiments of the present disclosure, the camera may be configured to generate a first image when the switch is in the first position, and the camera may be configured to generate a second image when the switch is in the second position. In some embodiments of the present disclosure, the system may further include a lock-in correlation that analyzes at least the first image and the second image to generate a third image.

Other objects, advantages, and novel features of the present invention will become apparent from the following detailed description of the invention when considered in conjunction with the accompanying drawings.

REFERENCE NUMERALS

| 100 | system |
| --- | --- |
| 110 | power supply and/or load |
| 120 | switch |
| 130 | device under test (DUT) |
| 140 | detector |
| 500 | method |
| 510 | applying a first condition |
| 520 | measuring a first luminescence |
| 530 | applying a second condition |
| 540 | measuring a second luminescence |
| 550 | comparing |
| 560 | generating |
| 600 | system |
| 610 | modulator |
| 620 | device under test (DUT) |
| 630 | signal |
| 640 | detector |

DETAILED DESCRIPTION

The present disclosure relates to methods of performing outdoor luminescence imaging of photovoltaic (PV) devices (e.g. cells, panels, and/or modules). Luminescence imaging is a valuable tool for detecting defects and/or nonuniformities in PV devices. The simplest method is electroluminescence (EL) imaging, in which the PV device is made to behave as an infrared light-emitting diode (LED), sinking power and emitting light, while a detector (e.g. camera) collects and measures the luminescence (e.g. resulting in the generation of an image). Luminescence is relatively weak in terrestrial non-concentrating PV devices, so EL imaging is almost always done in darkness.

PV cells, and the resultant PV panels and/or PV modules, luminesce at wavelengths near their band gap wavelength. Because the sun emits strongly in the same wavelengths, wavelength filtering alone cannot usually be used to separate the relatively weak luminescence signal emitted by the PV device from the background signal, which may be hundreds or thousands of times stronger. The dynamic range offered by most digital cameras (e.g. detectors), 14 bits to 16 bits, is normally not adequate to separate the signal emitted by the PV device from the background by subtracting a single pair of images. Even a pair of high-dynamic-range images would not suffice if they were taken using long exposure times during daylight, because outdoor illumination can vary significantly with time. Instead, as described herein, the luminescence signal emitted by the PV device may be varied (e.g. modulated) so it can be separated from the background signal using the repeated subtraction of pairs of images taken in close succession. This subtraction method is referred to herein as a "lock-in correlation".

Figure 1:
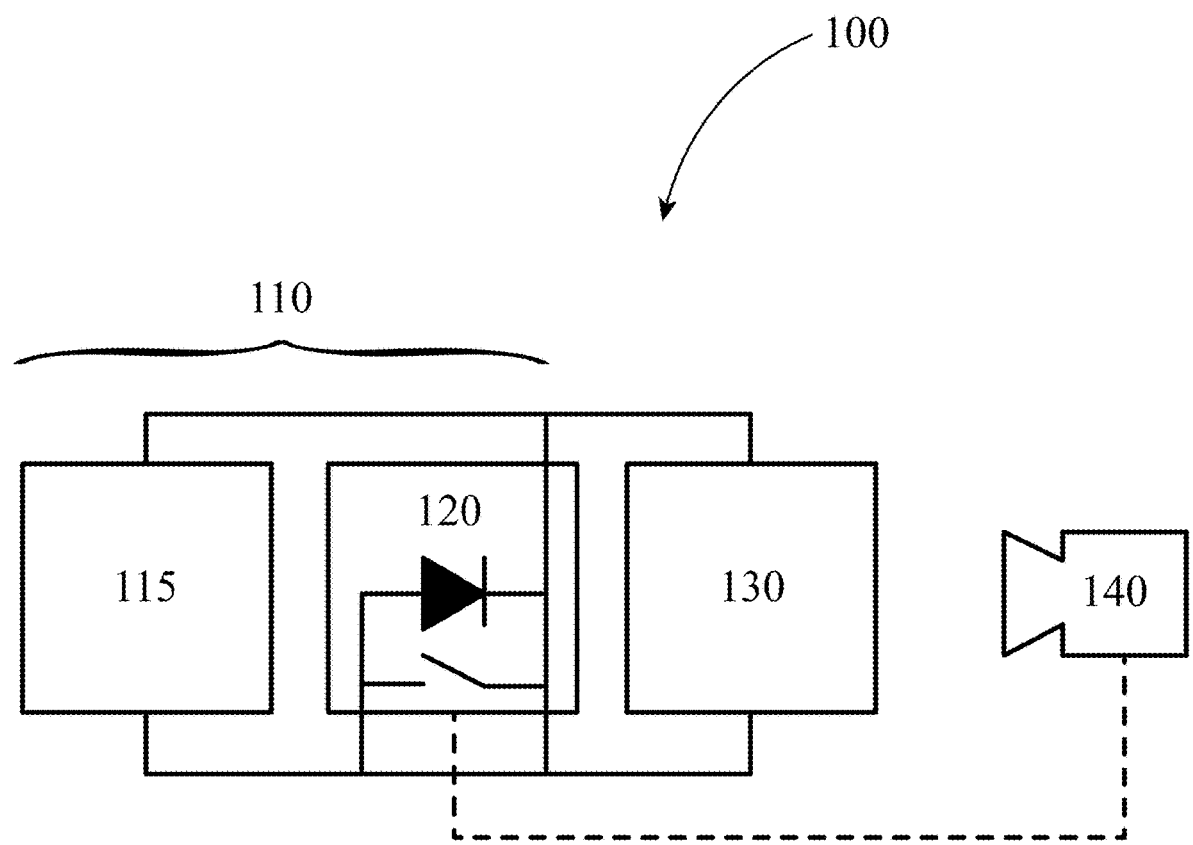
FIG. 1 illustrates a diagram of an apparatus that may be used for modulated luminescence imaging, according to some embodiments of the present disclosure.

FIG. 1 illustrates a system 100, according to some embodiments of the present disclosure, for measuring/detecting defects in a device under test (DUT) 130, for example a solar panel or module. In this example, the system 100 includes connecting in parallel a power supply and/or load 110 and a switch 120 to the DUT 130. Then, by varying the power supply and/or load 110 provided to the DUT 130, by repeatedly connecting and disconnecting the switch 120, the DUT 130 may be cycled between at least two different conditions, resulting in at least two levels of luminescence intensity from the DUT 130, which may be captured and measured by a detector 140 directed towards the emitting surface of the DUT 130. These luminescence intensities (light) may then by analyzed and quantified to generate images of the emitting surface of the DUT 130, to enable identification of defects, if defect exist in the DUT 130. Thus, in this example, the DUT 130 may be cycled between at least two conditions by a modulator 110, which includes both a switch 120 and a power supply and/or load.

Referring again to FIG. 1, accordingly, exemplary embodiments of the present disclosure provide methods for measuring and/or detecting defects and/or non-uniformities in PV devices (the DUT 130), where the methods include at least some of the following steps:

1) Put the DUT 130 into a first condition (Condition 1), by at least one of changing power input and/or power output supplied by the power supply and/or load 110, and or changing the position of the switch 120, resulting in a first luminescence intensity, which is relatively low;
2) Measure the first luminescence intensity emitted by the DUT 130 using a detector 140 to create a first image, called the "odd" image;
3) Put the DUT 130 into a second condition (Condition 2), by at least one of changing power input and/or power output supplied by the power supply and/or load 110, and or changing the position of the switch 120, resulting in a second luminescence intensity which is relatively high compared to the first luminescence intensity;
4) Measure the second luminescence intensity using the detector 140 to create a second image, called the "even" image;
5) Subtract the odd image from the even image, creating a "difference" image;
6) Add the difference image to a running total of difference images, called the "output" image; and
7) Repeat steps 1 through 6 until the output image has acceptable quality (e.g. contrast and/or resolution) or a target number of images is reached.

As described herein, in one example, an InGaAs camera (640×512 resolution, 14 bits dynamic range) was used as a detector to measure the luminescence generated by a PV device and to generate images of at least one surface of the PV device. The InGaAs detector used had a very high quantum efficiency (QE) in the wavelength range of interest (e.g. for a silicon solar cell DUT, 1000 nm to 1300 nm, or for a cadmium-telluride or gallium-arsenide solar cell DUT, 800 nm to 1000 nm). A Si detector may also be used, but with much longer acquisition times due to the lower QE of Si in the near infrared. In some embodiments of the present disclosure, an optical filter may be used to remove much of the background light outside the wavelength and/or wavelength ranges of interest. In some embodiments of the present disclosure, an optical filter may be a long pass filter, for example a 1000 nm long pass filter, or an 800 nm long pass filter, where the actual wavelength value of the filter determined by the luminescence spectrum of the DUT. In some embodiments of the present disclosure, each of the steps listed above may be performed manually or the steps may be at least partially automated using appropriate software.

As used herein, the term "modulating" refers to a switching between the two conditions of the DUT; e.g. between Condition 1 and Condition 2 and/or between Condition 2 and Condition 1 as shown above for Steps 1 and 3. Thus, as used herein, the term "modulator" refers to a device that affects the modulating of a DUT, the switching between the two conditions. In some embodiments of the present disclosure, a modulator may also trigger the detector to capture luminescence data corresponding to each condition (Condition 1 and Condition 2), enabling image acquisition/generation at a high frequency, such as between 1/60 Hz and 200 Hz, or between 1/60 Hz and 10 kHz, or at approximately 30 Hz. Thus, in some embodiments of the present disclosure, a modulator may synchronize switching a DUT between the two conditions with the actuation of the shutter of a camera (detector) that captures the luminescence intensities emitted by the DUT while in the two conditions, to generate images of the DUT to detect/identify defects present in the DUT.

Modulating may be accomplished by at least one of varying a power directed into the DUT and/or by varying a load that draws a power from the DUT. Thus, in some embodiments of the present disclosure, modulating (e.g. switching) may be achieved by modulating a power supply such as a DC PSU, for example, at least one of a benchtop DC power supply, a battery, and/or a PV device (cell, panel, and/or module) that is generating an electric current. In some embodiments of the present disclosure, modulating may be achieved by modulating a load such as a DC load (DCL), for example, a programmable electronic load, a variable resistor, and/or a fixed resistor. For either scenario, the modulating may be achieved by switching the power supply and/or the power load between a first condition (e.g. Condition 1) and a second condition (e.g. Condition 2). The switching between Condition 1 and Condition 2 may be an essentially instantaneous switch (e.g. a step function) between the two conditions, or there may be a finite period of time needed to transition between the two conditions; e.g. linear, non-linear, sinusoidal, etc. In some embodiments of the present disclosure, modulating may be achieved using at least one of a power supply and/or a power load in parallel with a switch, such as a MOSFET, a bipolar junction transistor, a silicon-controlled rectifier, a solid-state relay, an electromechanical relay, or a mechanical switch, and/or by connecting a MOSFET directly to the DUT in series. In some embodiments of the present disclosure, a MOSFET may include an intrinsic body diode, as shown in FIG. 1. In some embodiments of the present disclosure, a modulator may be a metal-oxide-semiconductor field-effect transistor (MOSFET), driven between a low-resistance and a high-resistance condition.

Four imaging techniques were applied to both of a c-Si module with cracked cells due to mechanical loading and a CIGS module with extensive shunting due to partial shade testing:
 1. indoor EL imaging;
 2. illuminated outdoor EL imaging;
 3. open-circuit outdoor PL (OCPL) imaging; and
 4. constant-current outdoor PL (CCPL) imaging.

For indoor EL imaging (Technique #1), the apparatus was configured as shown in FIG. 1, with a DC PSU in parallel with a switch (a MOSFET) and the DUT, in a dark room. The DC PSU was set to source the DUT's nameplate short-circuit current ($I_{sc}$). As used herein, short-circuit current ($I_{sc}$) is defined as defined in ASTM E1036. For this example, Condition 1 corresponded to the MOSFET switch short-circuiting both the DC PSU and the DUT, and Condition 2 corresponded to the DC PSU applying forward bias to the module. A single pair of images was collected, with a cumulative exposure time of 64 ms. Depending on the application, the exposure time may be between 100 μs and 60 seconds, or between 5 ms and 50 ms. To compare the three outdoor imaging techniques, 1000 pairs of images were collected for each technique. For these examples, a cumulative exposure time of 2.1 seconds was used for the c-Si module and 6.8 seconds for the CIGS module. Depending on the application, the cumulative exposure time may be between 0.21 seconds and 21 seconds, between 20 ms and 210 seconds, between 0.68 seconds and 68 seconds, or between 70 ms and 680 seconds. Total acquisition time, set by the 30 Hz framerate of the apparatus, was about 67 seconds for each test. However, depending on the application, the total acquisition time may be between 6.7 seconds and 670 seconds, or between 700 ms and 6700 seconds.

For illuminated outdoor EL imaging (Technique #2), the configuration was the same as for indoor EL imaging (Technique #1), except that Technique #2 was deployed outdoors in sunlight. For OCPL imaging (Technique #3), also tested in sunlight, the MOSFET switch was connected directly to the PV module, without a DC PSU or programmable DCL. In this configuration (Technique #3), Condition 1 may be completed with the MOSFET switch short-circuiting the DUT, whereas Condition 2 may be with the module at open circuit. For this example of Technique #3, the programmable DCL system was entirely battery-powered, which enabled the system to be portable and easy to use in the field. It is noted that although this example was performed outside in sunlight, the methods described herein may also be performed indoors or in a dark environment using an artificial light source.

For CCPL imaging (Technique #4), a programmable DCL was connected in parallel with the switch (e.g. MOSFET) and the DUT. In this example, the programmable DCL was configured to pass (draw from the module) a constant current of 0.7 $I_{sc}$. However, any suitable constant current draw may be used between 0.01 $I_{sc}$ and 0.99 $I_{sc}$ or between 0.5 $I_{sc}$ and 0.9 $I_{sc}$. In this configuration, Condition 1 was achieved with the switch short-circuiting both the DUT and the programmable DCL. Condition 2 was achieved with the module providing 0.7 $I_{sc}$ to the programmable DCL. Although for this example the programmable DCL was powered by a main power supply (e.g. plugged into an outlet), as mentioned above, a battery-powered DCL of a modulator may be used to vary the power to the PV device (e.g. solar cell, panel, and/or module) between Condition 1 and Condition 2. In this example, Condition 2 was essentially held at a constant value. However, in some embodiments of the present disclosure, one of the two conditions, for example Condition 2, may correspond to varying Condition 2 continuously between a first value and a second value. For example, for Technique #4, Condition 2 may be accomplished by varying the power draw between 0.01 $I_{sc}$ and 0.99 $I_{sc}$ or between 0.5 $I_{sc}$ and 0.9 $I_{sc}$. Thus, in some embodiments, depending the solar cell type (e.g. silicon, CIGS, CdTe, etc.), the size of the panel and/or module being tested, the $I_{sc}$ will vary depending on current density of DUT. In some embodiments of the present disclosure, current density of a DUT may range between 25 mA/cm$^2$ and 46 mA/cm$^2$; e.g. about 45 mA/cm$^2$ for a silicon DUT, and between about 25 mA/cm$^2$ 25 and about 35 mA/cm$^2$ for a CdTe DUT. Thus, depending on the surface area of the DUT, the $I_{sc}$ may vary between 2 A and 10 A at full sun. For the examples described herein, the $I_{sc}$ for the silicon module was about 8.5 A at full sun, and the $I_{sc}$ for the CIGS module was between about 2 A and 3 A at full sun.

The following discussion refers to the indoor EL images (from Technique #1; see FIGS. 2A and 4A) as a baseline for comparison with the outdoor methods (Techniques #2, #3, and #4; see FIGS. 2B-2D and FIGS. 4B and 4C). FIGS. 2A-D show output images for the c-Si module tested (DUT). The indoor EL image (FIG. 2A) shows that most cells contained at least one crack. Several cells had cracks that were partially or completely electrically isolating portions of those cells from the primary circuit of the solar panel. The illuminated outdoor EL image (obtained using Technique #2; see FIG. 2C) shows nearly all of the defects that were identified by the indoor method (Technique #1; see FIG. 2A). Substantially fewer than 1000 image pairs were utilized to obtain images having sufficient quality to be indistinguishable from those images shown in FIG. 2C. The minor differences between the indoor (Technique #1) and outdoor images Technique #2 may be attributable to module temperature differences between the indoor and the outdoor imaging sessions used for Technique #2, which can affect the appearance of cracked cells in resultant images.

Figure 2A:
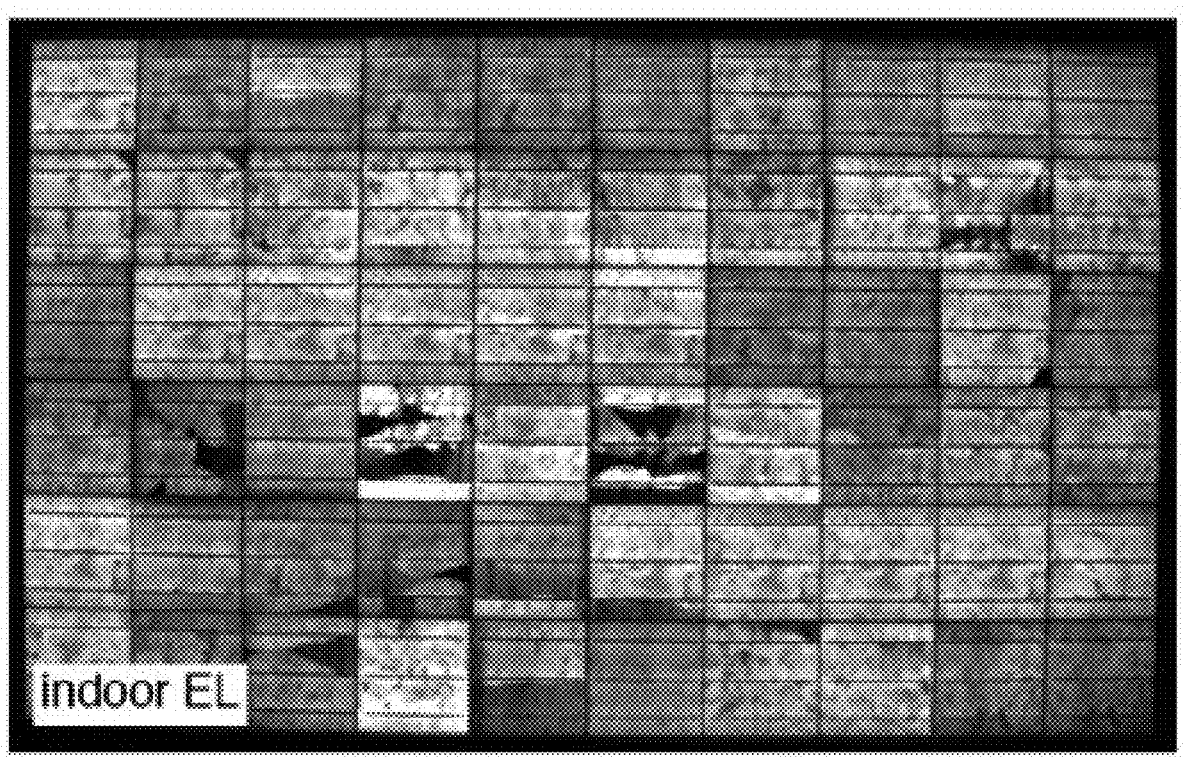
FIGS. 2A, 2B, 2C, and 2D illustrate images obtained from a crystalline silicon (c-Si) module, generated using systems and methods according to some embodiments of the present disclosure.
Figure 2B:
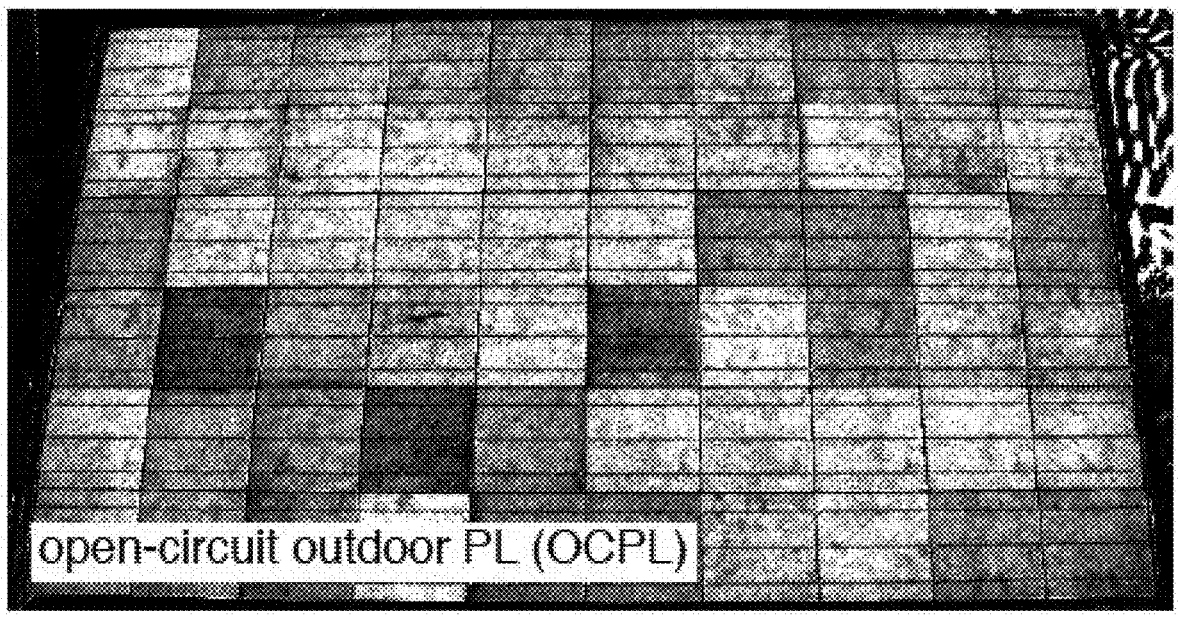
Figure 2C:
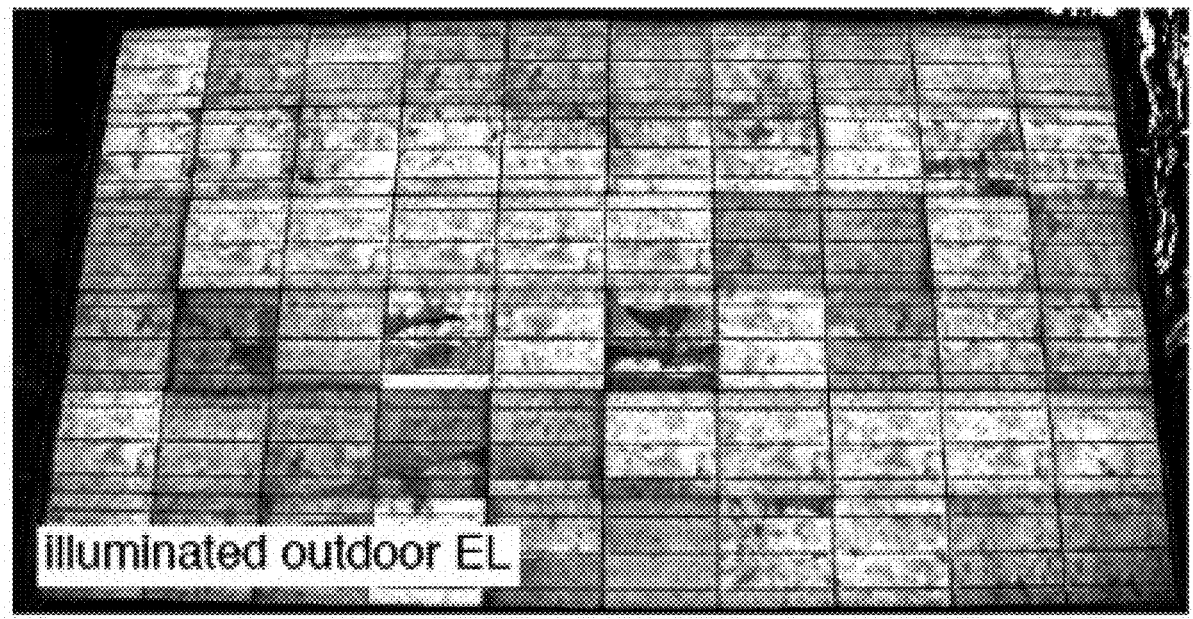
Figure 2D:
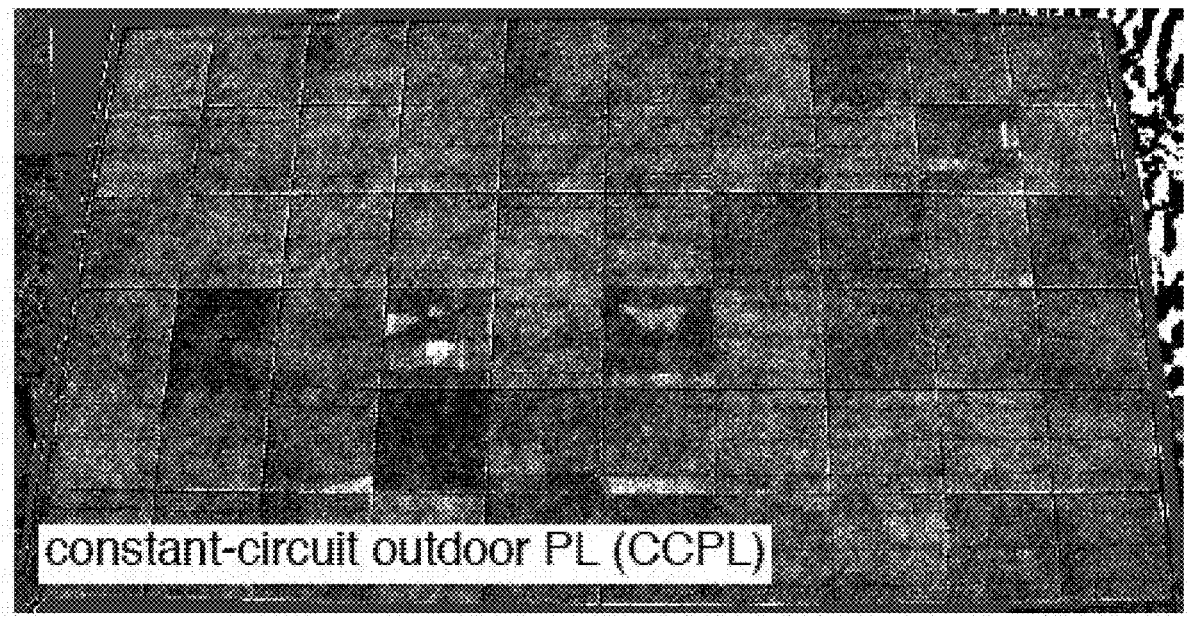

The OCPL image (obtained using Technique #3; see FIG. 2B) shows the characteristic luminescence pattern consisting of light emitting from solar cells, with some spots lighter and some darker. Contrast between cells can be due to mismatched cells and, within some cells, light and dark areas of the image may be due to spatial variation of lifetime. Cracks appear as thin dark lines, which are clearer when imaging a smaller area. However, the partially electrically isolated cell areas introduced by cracks, connected to the rest of the module through a high series resistance, do not appear in the OCPL (Technique #3) image. Instead, badly cracked cells appear uniformly dim. FIG. 2D shows that the CCPL method (Technique #4) caused these isolated areas to appear brighter than fully intact cells or intact portions of cracked cells. Because the difference between the Condition 1 and Condition 2 signals was small, the image resulting from Technique #4 was noisier than with the other techniques.

Figure 3A:
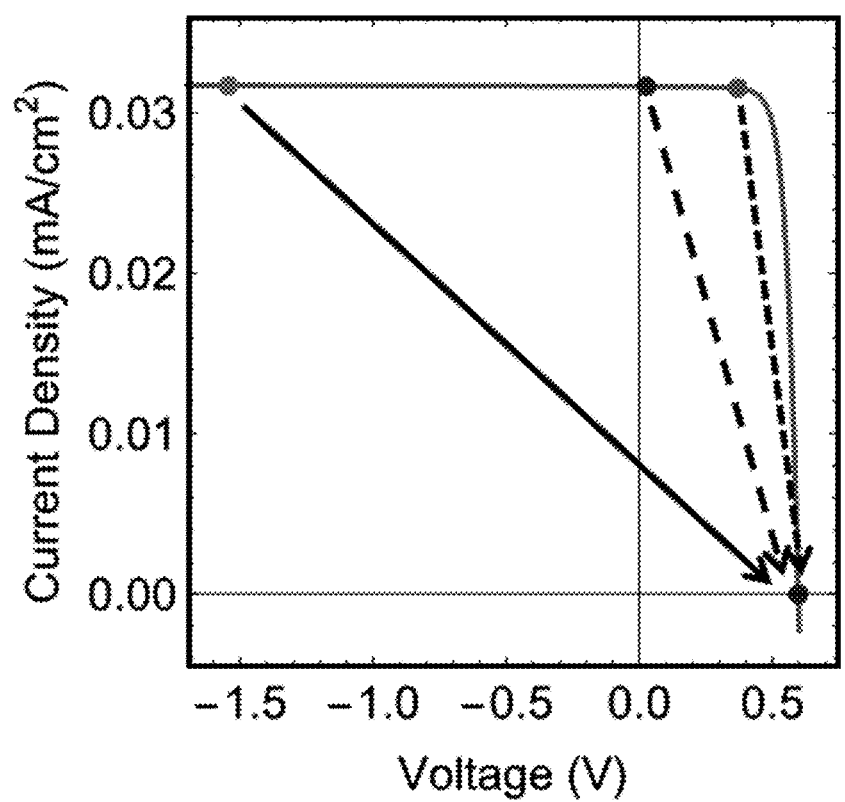
FIGS. 3A and 3B illustrate the principles of different methods of outdoor luminescence imaging on a module containing a cracked cell, according to some embodiments of the present disclosure.
Figure 3B:
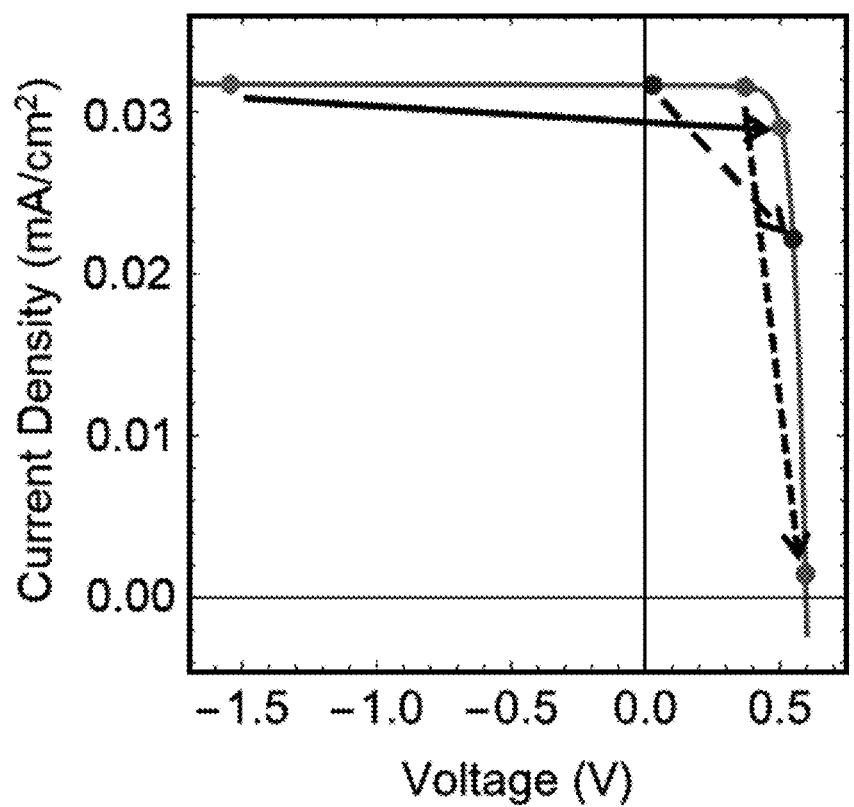

Without wishing to be bound by theory, FIGS. 3A and 3B explain the appearance of cracked cells with the different PL techniques, based on the simulated current density voltage (J-V) behavior of cells within a 60-cell module having a single damaged cell. FIG. 3A corresponds Technique #3 (OCPL) and FIG. 3B corresponds to Technique #4 (CCPL). In the simulation, which was based on first principle mathematical models with parameters tuned to the specific type of cell, one quarter of the damaged cell was isolated by a crack introducing a series resistance of 1Ω. The forward and reverse (J-V) characteristic was taken from measurements on a commercial polycrystalline cell. The solid lines correspond to intact regions of the module, the "long dashed" lines correspond to an intact full cell, and the "short dashed" lines correspond to isolated regions of the module. The arrows all point from Condition 1 to Condition 2. Because luminescence is high when extracted current density is low, the detected luminescence is proportional to the difference in current density between Condition 1 and Condition 2. The solid arrows are for OCPL (Technique #3), in which luminescence was detected for all regions. The dashed arrows are for CCPL (Technique #4), in which the isolated region remained bright because the series resistance of the crack keeps that region near $V_{oc}$ in Condition 2.

Referring again to FIG. 3A, the OCPL method (Technique #3), intact full cells, intact regions of broken cells, and isolated regions all luminesced weakly in Condition 1, then moved to open circuit (high luminescence) in Condition 2. The isolated region luminesced weakly in Condition 1 because the intact region is pushed into reverse bias to pass the $I_{sc}$ of the entire module. With the CCPL method (Technique #4), Condition 1 remained the same as with the OCPL method (Technique #3) but Condition 2 was changed to 0.7 $I_{sc}$. This change is enough to reduce the luminescence of the intact regions but left the Condition 2 luminescence of the isolated region high. This provided contrast, with the isolated regions appearing brighter.

Figure 4A:
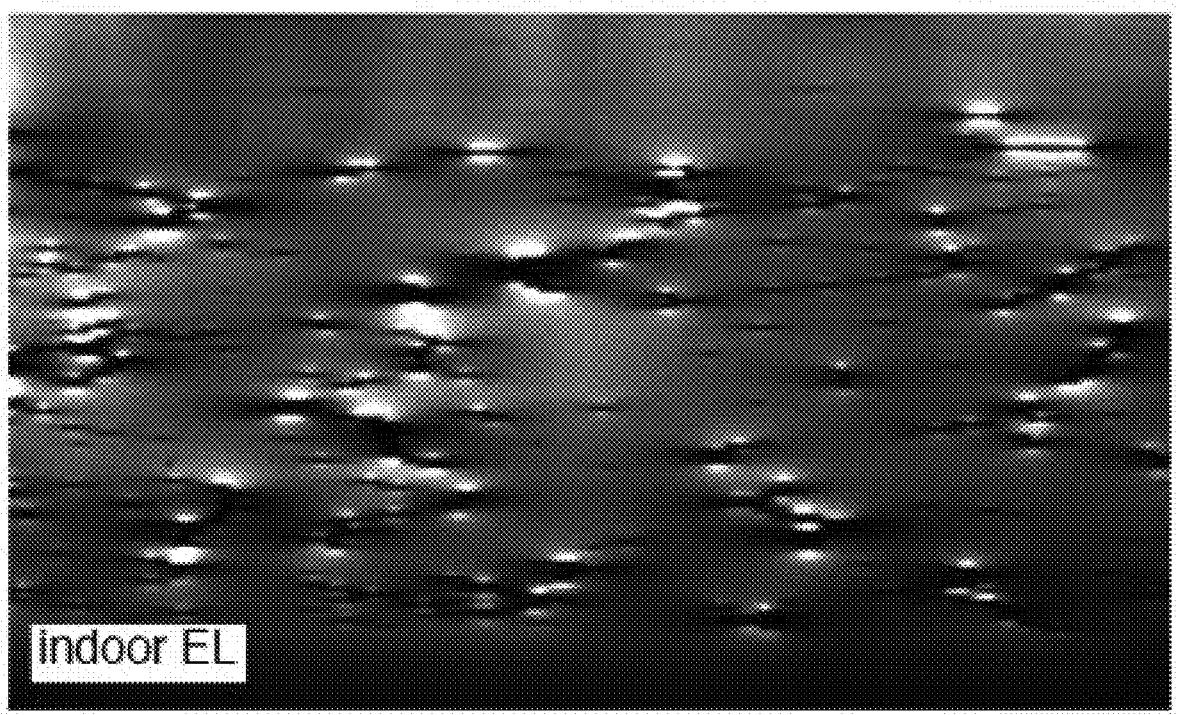
FIGS. 4A, 4B, and 4C illustrate images obtained from a CIGS module, generated using systems and methods according to some embodiments of the present disclosure.
Figure 4B:
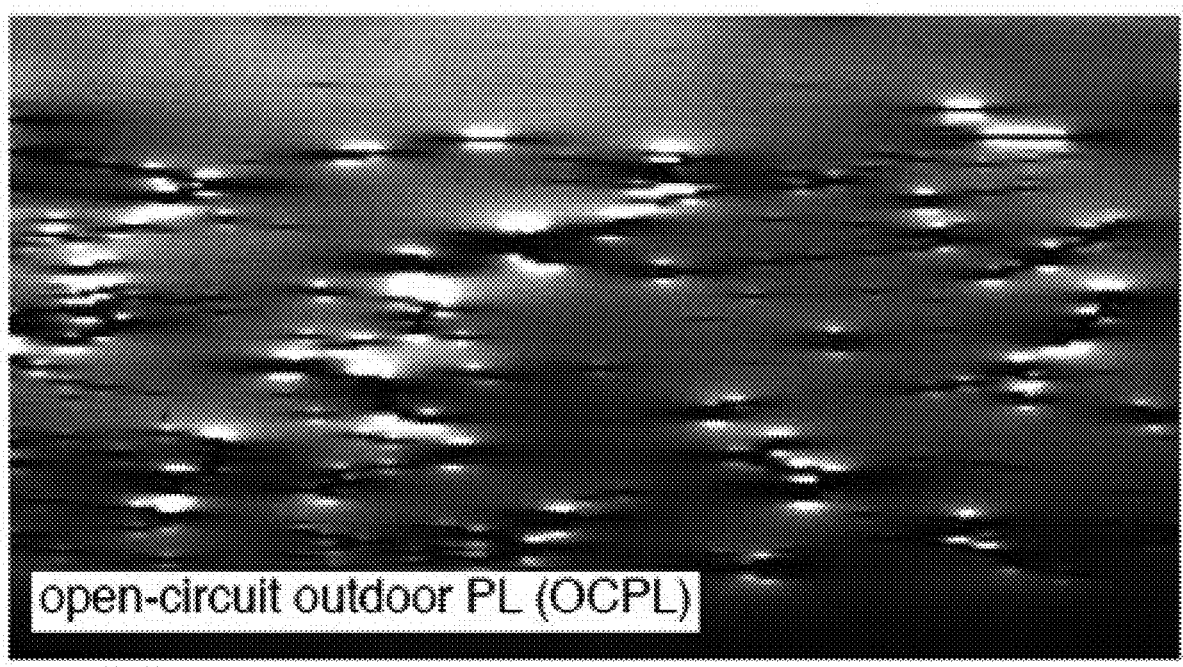
Figure 4C:
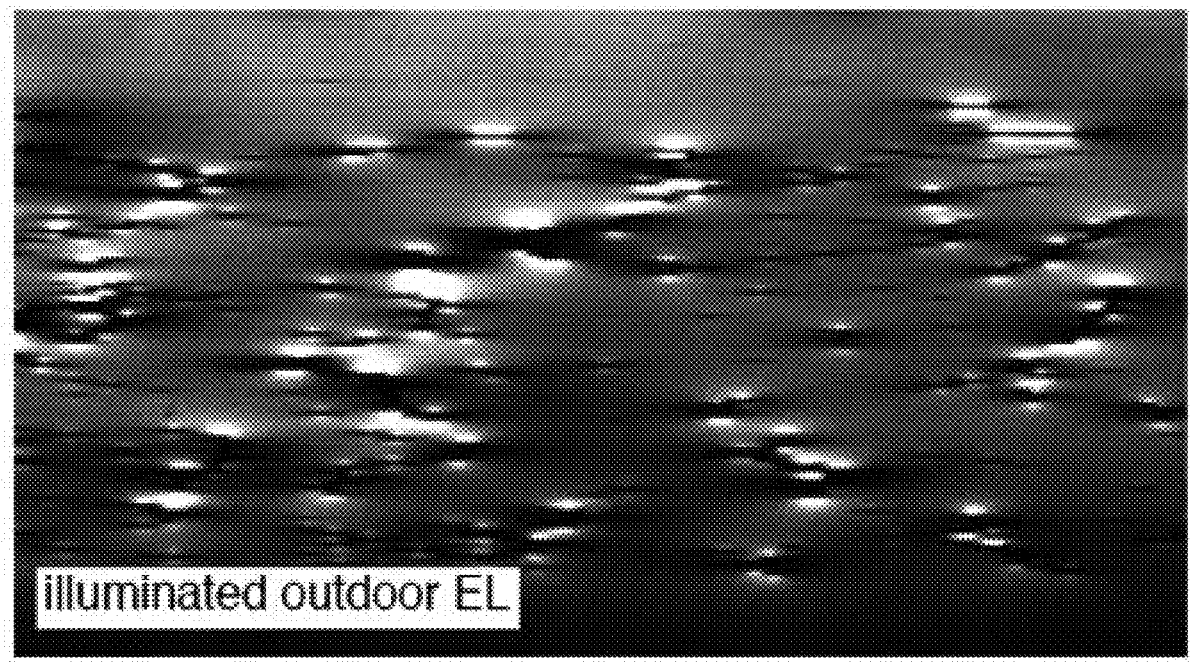

FIGS. 4A-C show images obtained from the CIGS module, using method and systems described herein, according to some embodiments of the present disclosure. The image obtained using the indoor EL method (Technique #1, see FIG. 4A) shows defective, shunted monolithic integration scribes (long dark areas surrounded by long light areas) and shunts formed during partial shade testing (short dark areas surrounded by short light areas). Minor large-scale nonuniformity in the device is visible across the top of the image, in an area that was not exposed to partial shade testing. The images result from the illuminated EL method (Technique #2; see FIG. 4C) and the OCPL method (Technique #3; see FIG. 4B) show an identical pattern of shunt defects. As with the c-Si module, fewer than 1000 image pairs are needed to reach very nearly the same image quality as shown here. The image obtained from the CCPL method (Technique #4) (image not shown) identified the same defects identified in the other three methods. Improvements to the images obtained by some of the methods described herein may be attained by tuning of the image acquisition (including exposure time, gain, optical filters) and the number of images collected.

To summarize, three imaging techniques (Techniques #2, #3, and #4) for use outdoors in sunny conditions are provided. These methods are useful for characterizing modules in the field, without the need to operate at nighttime or to disassemble and transport modules. As described herein, illuminated outdoor EL methods produce images of similar quality and showing identical defects compared to indoor EL images. OCPL, a technique that can easily be performed with portable, battery-operated equipment, produced high-quality images of cracks, shunts, and other types of nonuniformity. With the addition of a DC load, CCPL techniques produced images where areas of high series resistance appear brighter than surrounding areas.

Figure 5:
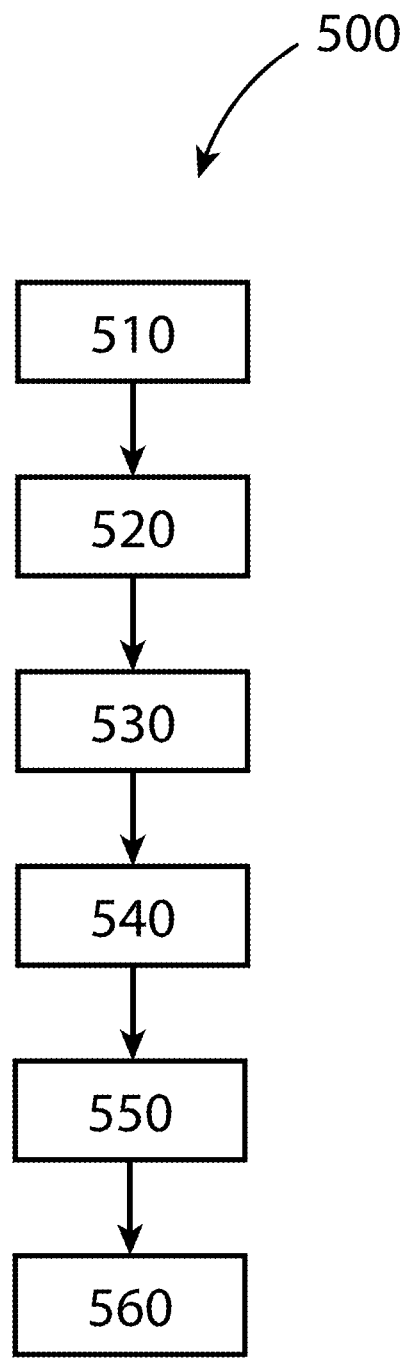
FIG. 5 illustrates a method for measuring and/or detecting defects in a photovoltaic device (e.g. cell, panel, and/or module), according to some embodiments of the present disclosure.

FIG. 5 summarizes a method 500 for measuring and/or detecting defects in a DUT (not shown); e.g. at least one of a solar cell, solar panel, and/or solar module, according to some embodiments of the present disclosure. In general, the method 500 includes applying a first condition 510 to the DUT, such that the DUT luminesces, with a detector (not shown) measuring the luminescence 520, the intensity of the light emitted by the DUT, while in the first condition. Then, the method 500 may proceed by applying a second condition 530 to the DUT, such that the DUT luminesces, with a detector (not shown) measuring the luminescence 540, the intensity of the light emitted by the DUT, while in the second condition. These steps may be repeated as many times as needed, to collect as many odd and even images as necessary, using lock-in correlation methods to create a sufficient number of difference images to produce an output image with sufficient resolution and/or contrast to identify defects within the emitting surface of the DUT. As described above, the DUT may be subjected to a power supply and/or a power load, where the first condition corresponds to a first level of the power supply and/or the power load, and the second condition corresponds to a second level of the power supply and/or the power load, where the second level is different from the first level. For example, in some embodiments of the present disclosure, the first condition may correspond to the short-circuit current, $I_{sc}$, of the DUT, whereas the second condition may correspond to some fraction of the $I_{sc}$.

Figure 6:
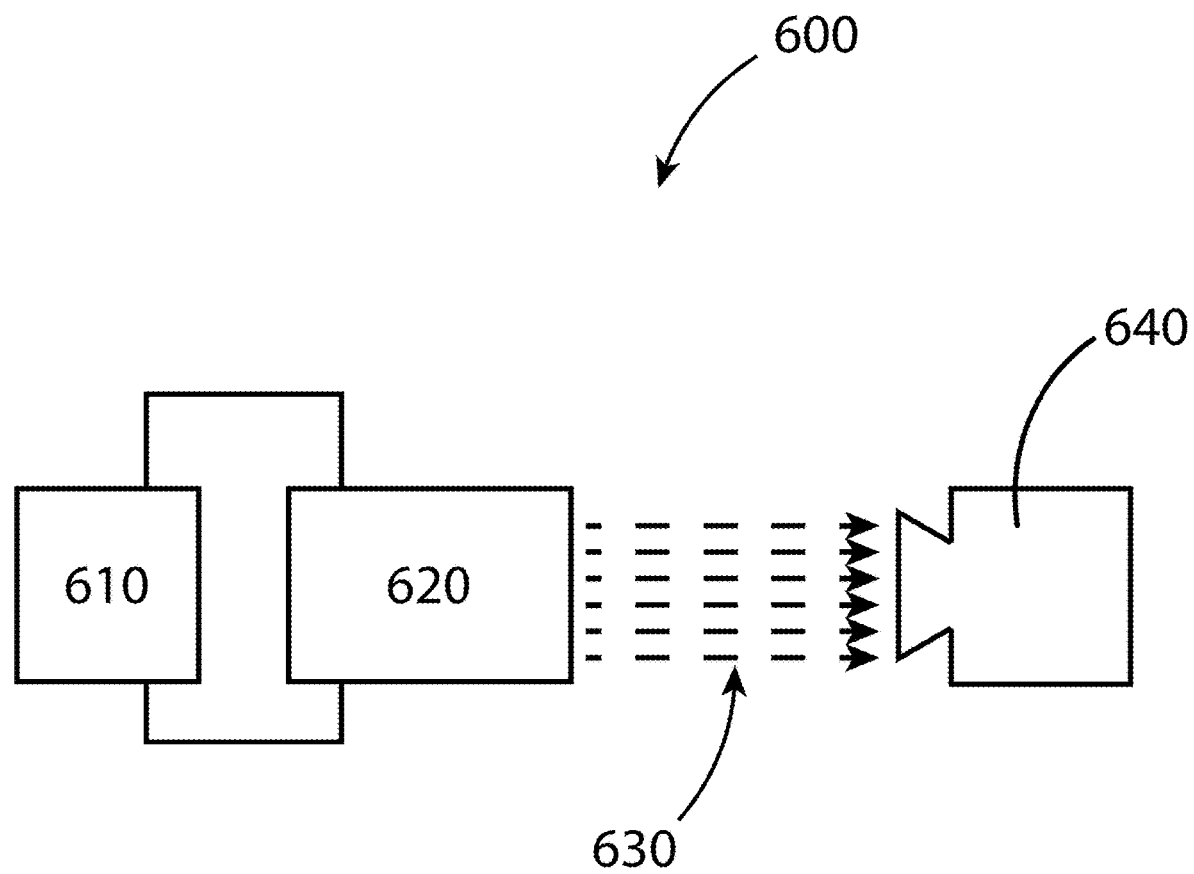
FIG. 6 illustrates a system for measuring and/or detecting defects in a photovoltaic device (e.g. cell, panel, and/or module), according to some embodiments of the present disclosure.

FIG. 6 summarizes a system 600 for measuring and/or detecting defects in at least one of a solar cell, solar panel, and/or solar module, according to some embodiments of the present disclosure. As described above, the system 600 may include a modulator 610 connected to the DUT 620, where a detector 640 is positioned to receive the light emitted by the DUT 620 while it is being cycled between the conditions of interest. Referring again to FIG. 1, in some embodiments of the present disclosure, a modulator (620 in FIG. 6), may include both a power supply and/or load and a switch. In some embodiments of the present disclosure, a modulator 610 may include only a switch or only a power supply and/or load. Advantages of such a system include, among other things, the ability to evaluate a DUT with less than $I_{sc}$ and/or using relatively lower power inputs to the DUT, evaluation of the DUT using either sunlight and/or artificial light, evaluation of the DUT either outside or inside, and the ability to detect defects in some DUTs under some conditions where other EL methods/systems fail.

EXAMPLES

Example 1

A method comprising: applying a first condition to a photovoltaic (PV) device; and applying a second condition to the PV device, wherein: the first condition results in a first luminescing of a surface of the PV device at a first intensity, the second condition results in a second luminescing of the surface at a second intensity, measuring the first intensity using a detector to create a first representation of the surface, measuring the second intensity using the detector to create a second representation of the surface, and comparing the first representation with the second representation to create a third representation of the surface that identifies a defect in the surface.

Example 2

The method of Example 1, wherein the applying the first condition comprises applying a first current to the PV device.

Example 3

The method of Example 2, wherein: the applying the second condition comprises applying a second current to the PV device, and the second current is different from the first current.

Example 4

The method of Example 1, wherein the applying the first condition comprises drawing a third current from the PV device.

Example 5

The method of Example 4, wherein: the applying the second condition comprises drawing a fourth current from the PV device, and the fourth current is different from the third current.

Example 6

The method of Example 5, wherein the first current is achieved by short-circuiting the PV device, such that the first current is equal to the short-circuit current ($I_{sc}$) of the PV device.

Example 7

The method of Example 6, wherein the second current is achieved by regulating the second current to a value between $0.01\ I_{sc}$ and $0.99\ I_{sc}$.

Example 8

The method of Example 7, wherein the value is between $0.5\ I_{sc}$ and $0.9\ I_{sc}$.

Example 9

The method of Example 7, wherein the value is between 2 A and 10 A.

Example 10

The method of Example 9, wherein the value is between 2 A and 3 A.

Example 11

The method of Example 7, wherein the value is substantially fixed.

Example 12

The method of Example 7, wherein: the second current corresponds to varying the second current between $0.01\ I_{sc}$ and $0.99\ I_{sc}$, and the second measuring is performed during at least a portion of the varying.

Example 12

The method of Example 1, wherein the applying the first condition comprises applying a light having a first power input to the surface.

Example 13

The method of Example 12, wherein: the applying the second condition comprises applying a light having a second power input to the surface, and the second power input is different than the first power input.

Example 14

The method of Example 1, wherein the third representation is an image of the surface.

Example 15

The method of Example 1, further comprising: a first switching between the first applying and the second applying; and a second switching between the second applying and the first applying, wherein: the first condition is maintained for a first period of time, after the first period of time has ended, the first switching occurs, the second condition is maintained for a second period of time, after the second period of time has ended, the second switching occurs, and the first switching and the second switching are repeated between 1 and 1000 occurrences.

Example 16

The method of Example 15, wherein the first period of time is between 100 μs and 60 seconds.

Example 17

The method of Example 15, wherein the second period of time is between 100 μs and 60 seconds.

Example 18

The method of Example 1, wherein at least one of the first luminescing or the second luminescing produces light comprising a wavelength between 800 nm and 1300 nm.

Example 19

The method of Example 18, wherein the wavelength is between 1000 nm and 1300 nm.

Example 20

The method of Example 18, wherein the wavelength is between 800 nm and 1000 nm.

Example 21

The method of Example 18, further comprising filtering at least a portion of the light.

Example 22

The method of Example 21, wherein the filtering passes light having a wavelength greater than or equal to 800 nm.

Example 23

The method of Example 21, wherein the filtering passes light having a wavelength greater than or equal to 1000 nm.

Example 24

The method of Example 1, wherein the applying the first condition and the applying the second condition are performed while the surface is exposed to sunlight.

Example 25

A system comprising: a switch; and a detector, wherein: the switch is configured to be electrically connected to a photovoltaic (PV) device, the PV device is configured to generate a current, the switch has a first position that results in the PV device being short-circuited, resulting in a short-circuit current, $I_{sc}$, and the switch has a second position that results in the PV device providing a current, I, where $0 \leq I < I_{sc}$.

Example 26

The system of Example 25, wherein the switch comprises at least one of a MOSFET, a bipolar junction transistor, a silicon-controlled rectifier, a solid-state relay, an electromechanical relay, or a mechanical switch.

Example 27

The system of Example 25, wherein the switch is connected in series with the PV device.

Example 28

The system of Example 25, further comprising at least one of a power supply or a power load, wherein the power supply or the power load, and the switch are electrically connected to the PV device in parallel.

Example 29

The system of Example 28, wherein the power load comprises at least one of a direct current load, a programmable electronic load, a variable resistor, or a fixed resistor.

Example 30

The system of Example 29, wherein the power load comprises a battery-powered direct current load.

Example 31

The system of Example 28, wherein the power supply comprises a direct current power supply unit.

Example 32

The system of Example 25, wherein the detector comprises at least one of an Si camera or an InGaAs camera.

Example 33

The system of Example 32, further comprising a long pass filter.

Example 34

The system of Example 32, wherein: the camera is configured to generate a first image when the switch is in the first position, and the camera is configured to generate a second image when the switch is in the second position.

Example 35

The system of Example 34, further comprising a lock-in correlation that analyzes at least the first image and the second image to generate a third image.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:
1. A method comprising:
applying a first condition to a photovoltaic (PV) device;
applying a second condition to the PV device;
a first switching between the first applying and the second applying; and a second switching between the second applying and the first applying, wherein:

the first condition is maintained for a first period of time, after the first period of time has ended, the first switching occurs, the second condition is maintained for a second period of time, after the second period of time has ended, the second switching occurs, the first switching and the second switching are repeated between 1 and 1000 occurrences, the first condition results in a first luminescing of a surface of the PV device at a first intensity, the second condition results in a second luminescing of the surface at a second intensity, measuring the first intensity using a detector to create a first representation of the surface, measuring the second intensity using the detector to create a second representation of the surface, and comparing the first representation with the second representation to create a third representation of the surface that identifies a defect in the surface.

2. The method of claim 1, wherein the applying the first condition comprises applying a first current to the PV device.

3. The method of claim 2, wherein:

the applying the second condition comprises applying a second current to the PV device, and the second current is different from the first current.

4. The method of claim 1, wherein the applying the first condition comprises drawing a third current from the PV device.

5. The method of claim 4, wherein:

the applying the second condition comprises drawing a fourth current from the PV device, and the fourth current is different from the third current.

6. The method of claim 3, wherein the first current is achieved by short-circuiting the PV device, such that the first current is equal to the short-circuit current ($I_{sc}$) of the PV device.

7. The method of claim 6, wherein the second current is achieved by regulating the second current to a value between 0.01 $I_{sc}$ and 0.99 $I_{sc}$.

8. The method of claim 7, wherein:

the second current corresponds to varying the second current between 0.01 $I_{sc}$ and 0.99 $I_{sc}$, and the measuring of the second intensity is performed during at least a portion of the varying.

9. The method of claim 1, wherein at least one of the first luminescing or the second luminescing produces light comprising a wavelength between 800 nm and 1300 nm.

10. The method of claim 9, further comprising filtering at least a portion of the light.

11. The method of claim 1, wherein the applying the first condition and the applying the second condition are performed while the surface is exposed to sunlight.

* * * * *